United States Patent [19]
da Costa

[11] 3,939,830
[45] Feb. 24, 1976

[54] MANUALLY OPERABLE DECHOKING AND RESUSCITATING DEVICE

[76] Inventor: Harry da Costa, 5925 Foothill Drive North, Scottsdale, Ariz. 85253

[22] Filed: Mar. 10, 1975

[21] Appl. No.: 557,111

[52] U.S. Cl............................... 128/145.7; 128/278
[51] Int. Cl.².......................................... A61M 16/00
[58] Field of Search........... 128/145.7, 145.5, 145.6, 128/145.8, 276, 278

[56] References Cited
UNITED STATES PATENTS

| | | | |
|---|---|---|---|
| 2,428,451 | 10/1947 | Emerson........................... | 128/145.7 |
| 3,158,152 | 11/1964 | Bloom.............................. | 128/145.5 |
| 3,185,147 | 5/1965 | Champagne...................... | 128/145.5 |

*Primary Examiner*—Robert W. Michell
*Assistant Examiner*—Henry J. Recla
*Attorney, Agent, or Firm*—John A. Robertson

[57] ABSTRACT

A manually operable device susceptible of use as a de- choker for removing an obstruction from the throat of a person, generating artificial respiration, or alleviating a heart failure by applying pressure from the lungs to the heart to compress the latter and cause some blood circulation. The device consists essentially of a face mask, a cylinder having an open end, and an end wall connected to the mask with the mask and end wall having aligned openings, a spring biased piston reciprocal in the cylinder with a rod connected thereto and a handle on the end of the rod, a frame on the cylinder presenting a crossbar spaced from the handle whereby the crossbar and handle may be grasped by the hand of an operator, a one-way check valve in the cylinder end wall, a removable detent for said valve, and a safety valve on said piston which opens when the suction effect of the piston reaches a safe limit. A perforated tube is connected to the mask in connection with the opening therein and is of a length providing for its insertion between the teeth of a patient when the mask is applied to his face. This tube functions as a gag and a tongue depressor.

10 Claims, 7 Drawing Figures

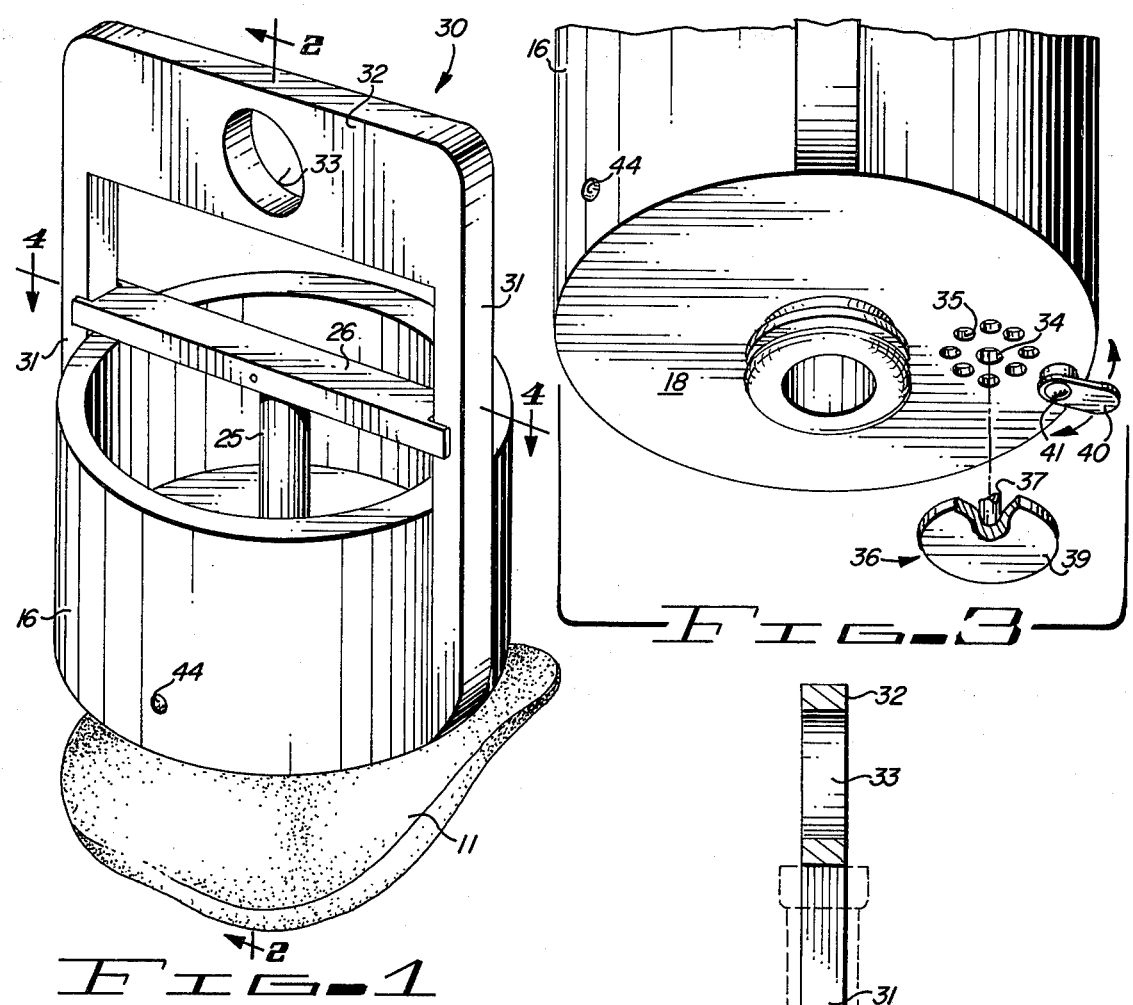
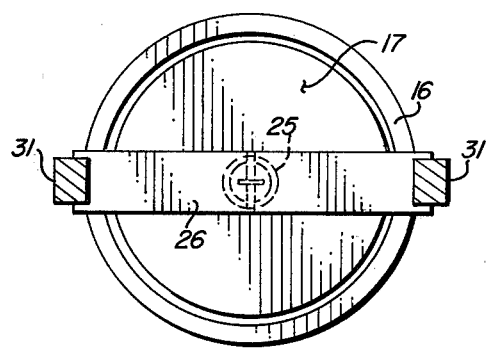
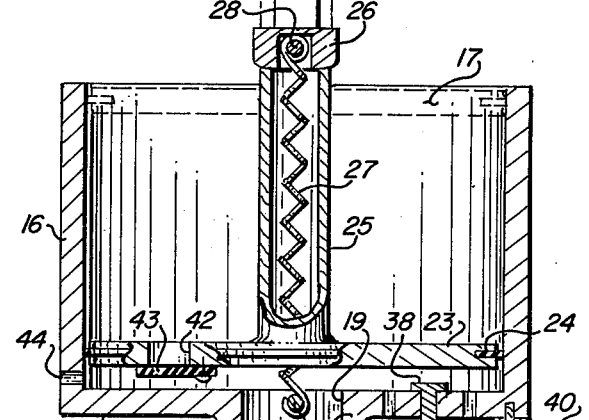
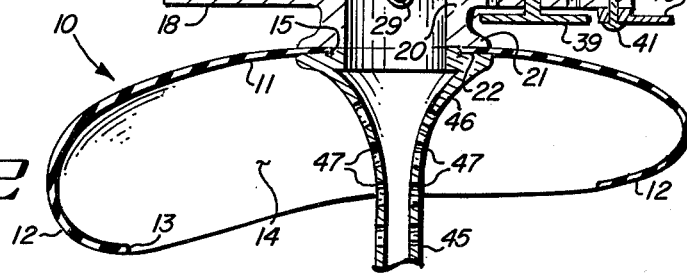

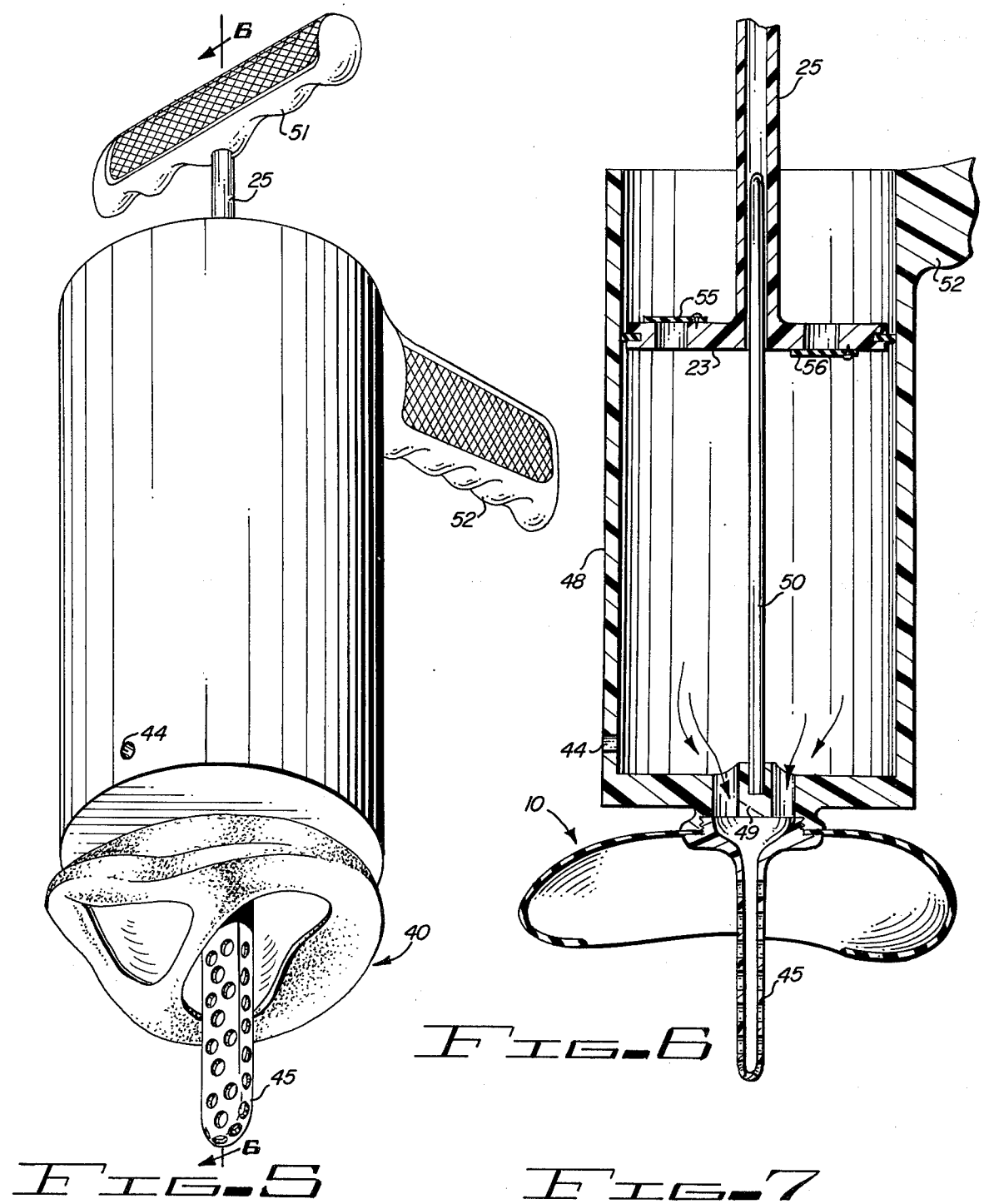

MANUALLY OPERABLE DECHOKING AND RESUSCITATING DEVICE

The present invention relates to the removal of a throat obstruction, artificial respiration and the alleviation of a heart failure. The invention is concerned primarily with a manually operable device which by a simple operation may be adapted for use as a dechoker or a resuscitator and by a change in the size of a cylinder rendered suitable for use to apply pressure to the heart of a patient from the lungs to generate circulation of blood to a small degree.

BACKGROUND OF THE INVENTION

For a long time people have been subjected to the possibility of choking to death from an obstruction in the throat which inhibits breathing. Such an obstruction is usually a piece of food of a size which literally closes off the throat. At the present time the public has been alerted to this danger by instances of people dying in the rest rooms of restaurants or at home. It is, of course, easy to remove such an obstruction in the emergency room of a hospital where adequate equipment is available. However a customer of a restaurant or a person at home will ordinarily not have immediate access to such equipment and there is now no known device which is particularly adapted to be maintained available in the rest rooms of commercial establishments or the home and is so simple that it may be operated with ease and facility. In many cases the choking person has died in transit to a hospital.

Many people suffer from impairment of their respiration by being immersed under water for a long time, from the smoke of a burning building or other causes. Rescue workers in attempt to literally bring such a person back to life have resorted to artificial resuscitation by mouth to mouth respiration. The prior art embraces many examples of devices for either replacing mouth to mouth respiration or facilitating this operation. However it is believed that there is no simple device which is capable of use as a dechoker and which by an easy operation converts to use for artificial respiration.

When a person suffers from a heart failure, whatever its cause, circulation of the blood ceases and if this occurs for a prolonged period the person dies. It is now a well recognized fact that a heart may be started in its pumping action to circulate blood by alternately applying and relieving pressure to and from the heart. Thus many qualified rescue workers have resorted to massaging an exposed heart to start the blood circulating.

One facet of the present invention is founded on the belief that if sufficient air pressure is built up in the lungs it will be effective on the heart, which is closely adjacent to the lungs, to compress the heart and when the pressure is relieved or rendered negative the heart will expand to its normal condition. It is believed that there is now no known device that is adapted to be kept available in public places such as rest rooms, swimming pools, beaches and the like which will supply sufficient air under pressure to the lungs of a person undergoing a heart failure to start blood circulation. This belief is emphasized as to a manually operable device which, with exception of changes in dimension comprises the essential elements of a dechoker and resuscitator.

OBJECTS OF THE INVENTION

With the foregoing conditions in mind the present invention has in view the following objectives:

1. To provide a manually operable device for removing an obstruction from the throat of a person by creating a suction or vacuum condition in the throat on the external side of the obstruction.

2. To provide a device of the type noted which by a simple operation is converted to use for artificial respiration by alternately introducing air under pressure to the lungs and withdrawing air from the lungs by suction.

3. To provide a manually operable device of the character aforesaid which includes the essential elements of the resuscitator mentioned in the second object with the dimensions of certain elements enlarged to provide for the delivery of an adequate amount of air under pressure to the lungs to compress the heart and generate blood circulation.

4. To provide a device of the kind described in which air pressure is created by a pump of the cylinder and piston type and in which the piston has a safety valve to prevent an unsafe vacuum condition being engendered on the suction stroke of the piston.

5. To provide, in a device of the type noted, a face mask that is applied over the nose-chin area of a person and from which projects a tube that extends into the mouth between the teeth and over the tongue of the person to whom the mask is applied whereby it functions as a gag and a tongue depressor; and 6. To provide, in a device of the character aforesaid, a pump of the piston type which is susceptible of operation by a single hand of an operator whereby the other hand of said operator is free and available for use in urging the mask against a person's face to create an airtight seal therewith.

Various other objects and advantages of the invention such as arise in carrying out the above ideas in a practical embodiment, will in part become apparent, and in part be hereinafter stated as the description of the invention proceeds.

SUMMARY OF THE INVENTION

The foregoing objects are achieved by providing a device comprising a flexible face mask designed to fit over the nose-chin area of a person and presenting a cavity defined by a peripheral edge which is pressed against the face of the person to create an airtight seal. A rigid cylinder having an open end and an end wall is attached to the mask with the end wall engaging the mask and having a central opening in alignment with an opening in the mask. A piston in the form of a plate or disc is reciprocal in the cylinder.

Upstanding from one face of the piston is a rod which projects a small distance beyond the open end of the cylinder. Secured to the outer end of this rod is a handle in the form of a transverse member that is adapted to be engaged by the fingers of an operator. The rod is tubular and housed therein is an expansion coil spring having one end secured to the outer end of the rod and its other end anchored to the end wall. This spring biases the piston towards the end wall.

A U shaped frame is mounted in an inverted position on the cylinder. This frame has a pair of legs secured to the exterior of the cylinder and extends an appreciable distance beyond the open end of the cylinder. Extending between the outer ends of these legs is a crossbar substantially parallel to the transverse member on the piston rod. This crossbar is engaged by the palm of the hand of an operator whose fingers engage the transverse member at the same time. Thus the piston is moved outwardly by the operator tightening his grip over the crossbar and transverse member and permitted to be moved inwardly under the influence of the spring by loosening his grip.

The end wall of the cylinder is formed with a small aperture offset from the central opening therein and spaced thereabout are a plurality of air passages. A one-way check valve is moveably mounted in the aperture and has a lower head in the form of small disc that closes the air passages when this disc engages the underface of the end wall. The disc is moved into position closing the air passages on the outstroke of the piston by suction and into open position of the instroke by air pressure. A swinging detent is pivotally mounted on the underside of the end wall and is swung into engagement with the valve disc to hold the latter in closed position when the device is used for artificial respiration.

A small bleed hole, such as one in the order of 3/32 inch diameter is formed in the cylinder closely adjacent to the end wall. This bleed hole supplies air for artificial respiration. but its size does not materially impair the suction effect when the device is used for dechoking purposes. The piston is formed with an orifice offset from the piston rod which is controlled by a safety valve in the form of a flap mounted on the inner face of the piston adjacent to this orifice.

Secured to the inner or face confronting side of the mask is a perforated tube which extends from a mask sufficiently to provide for its insertion between the teeth of a person to the face of whom the mask has been applied. This tube functions as a gag to prevent the person from closing or clenching his teeth as from a spasm and also as a tongue depressor.

When the device is designed for the alleviation of a heart failure by causing blood circulation the size of the cylinder is increased to a capacity of about 6 liters. As this increase in size will require a longer stroke of the piston certain minor alterations are made in the piston cylinder mechanism as by providing a guide rod for the piston, the handle arrangement, and safety valves on the piston.

For a full and more complete understanding of the invention reference may be had to the following description and accompanying drawings wherein:

FIG. 1 is a perspective of a portion of the face mask and the piston pump connected thereto.

FIG. 2 is a vertical section taken on the plane of the line 2—2 of FIG. 1.

FIG. 3 is a perspective looking at the underside of the piston and depicting the one-way check valve in exploded relation.

FIG. 4 is a horizontal section taken on the plane of the line 4—4 of FIG. 1.

FIG. 5 is a perspective of the device as modified for alleviation of a heart failure.

FIG. 6 is a vertical section on the plane of the line 6—6 of FIG. 5; and

FIG. 7 is a phantom outline of a person suffering from a heart failure with whom the device of FIG. 5 and 6 is intended to be used.

DESCRIPTION OF THE PREFERRED EMBODIMENT

Referring now to the drawings wherein like elements are identified by the same reference characters throughout the several views and first more particularly to FIGS. 1 to 4 a face mask is referred to in its entirety at 10 (FIG. 2). It is of a flexible plastic, such as rubber and comprises a main body portion 11 which is integrally joined to a concave wall 12 terminating in a free edge 13. The mask structure described is dimensioned to fit over the nose-chin area of the face of a person leaving a cavity 14 between body portion 11 and the face to which it is applied. The marginal areas immediately adjacent to edge 13 are urged against the face to form an airtight seal therewith. Body portion 11 is formed with an opening 15.

A cylinder 16 of a rigid plastic has an open end 17 and its other end is closed by an end wall 18. The latter is formed with a central opening 19 and aligning with opening 15 in body portion 11 of the mask. While any of several arrangements may be provided to secure end wall 18 to mask 10 one such arrangement is shown in FIG. 2. Thus a neck 20 depends from end plate 18 about opening 19 and has a lower end portion 21 of increased thickness formed with an annular grove 22 which receives the marginal portion of body 11 at hole 15.

A piston 23 in the form of a metallic plate or disc is fitted for reciprocation in cylinder 16. Simple engagement of the peripheral edge of piston 23 with the bore of the cylinder may be adequate to afford the airtight relation required but a piston ring 24 is provided for this purpose in accordance with accepted practice in the pump art.

Upstanding from the outer or upper face of piston 23 at the center thereof is a tubular rod 25. Secured to the upper end of rod 25 is a handle or finger engageable member 26 which is normal to rod 25 and closes the upper end of the bore of the latter. An expansion coil spring 27 is disposed in rod 25 with its upper end anchored to member 26 as indicated at 28 and its lower end to end wall 23 by a cross pin 29 extending across opening 19. Spring 27 biases piston 23 inwardly towards end wall 18.

An inverted U shaped frame is designated generally 30. It comprises a pair of legs 31 lower portions of which are secured to the outer surface cylinder 16 as illustrated in FIG. 1. The outer ends of legs 31 are spanned by a crossbar 32 formed with a central hole 33. Crossbar 32 is parallel to cross member 26 which enables an operator to simultaneously grasp these two elements with one hand thereby leaving his other hand free to press mask 10 against a person's face. This is accomplished by placing the palm of the hand over crossbar 32 and the fingers under handle member 26. If convenient the thumb may be inserted in opening 33 rather than using the palm to grip crossbar 32.

Referring now to FIG. 3 end wall 18 is shown as formed with an aperture 34 which is surrounded by a plurality of air passages 35 circularly arranged. A valve member having a structure similar to a conventional collar button is identified generally at 36. It cooperates with air passages 35 to provide a one-way check valve. Thus valve 36 comprises a stem 37 that is slidably received in aperture 34. A stop 38 is formed on the upper end of stem 37 and engages the upper surface of end wall 18 to limit downward movement of valve 36 and maintain the latter assembled in end wall 18 (see FIG. 2). A disc like head 39 on the lower end of the stem 37 is dimensioned to cover air passages 35 when valve 36 is in its uppermost position. It is evident that on an instroke of piston 23 valve 36 moves inwardly under air pressure to open passages 35. On the outstroke of piston 23 valve 36 is moved outwardly by suction to close passages 35.

A detent is shown at 40. It is pivotally mounted at 41 on the underface of end wall 18 whereby it is adapted to be swung into and out of position engaging head 39. When so engaged valve 36 is held in closed position. Thus the device is adapted for artificial respiration.

Piston 23 is formed with an orifice 42 (FIG. 2) offset from its center. Secured to the inner face of piston 23 adjacent to orifice 42 is a flap valve 43 which, together with the orifice constitutes a safety valve. Flap valve 43 is flexible to a predetermined degree so as to open when a safe limit of the vacuum condition created by an outstroke of piston 23 is reached.

Cylinder 16 is formed with a small bleed hole 44 adjacent to end wall 18. Hole 44 has a diameter in the order of 3/32 inch. Thus air is supplied to cylinder 16 for respiratory purposes but the creation of a vacuum condition on the outstroke of piston 23 is not materially impaired.

A tube 45 of a material which preferably is rigid or slightly flexible has an enlarged or bell shaped end portion 46 which is connected to the lower end of neck 20. This connection is illustrated as being integral. Tube 45 has perforations 47 and is of a length which provides for it being inserted between the teeth and over the tongue of a person to whom the mask 10 is fitted. Thus if the person should, under spasm, exhibit a tendency to clench his teeth tube 45 prevents closing of the mouth. It also acts as a tongue depressor to hold the tongue in a position in which it cannot block the throat.

OPERATION OF THE PREFERRED EMBODIMENT

While the mode of operation and means of using the above described device are believed to be obvious from the illustrations of the drawings and description of the elements they are briefly outlined as follows:

If a person has an obstruction in his throat that requires immediate removal he is positioned with his head and trunk bent forwardly, preferably at an angle of 45° whereupon an operator first swings detent 40 out of engagement with valve head 39. With one hand he grasps handle member 26 and crossbar 32 and with the other hand places mask 10 over the nose and mouth of the person 16 then tightens his grip on member 26 and crossbar 32 to generate an outstroke of piston 23. This creates a vacuum condition in cylinder 16 which closes passages 35 and the vacuum becomes effective in the throat of the person. This causes air pressure from the lungs and/or partial regurgitation of the stomach contents to eject the obstruction or at least move it partially outwardly in the throat.

If the obstruction is not completely removed the operator loosens his grip which permits spring 27 to move piston 23 inwardly. This inward movement is not effective on the obstruction because valve 36 is moved into position opening passage 35. Moreover, bleed hole 44 permits but limits the rate of inhalation to that which cannot cause return propulsion of the obstruction. The cycle of operation is repeated until the obstruction is removed.

Hole 33 in crossbar 32 constitutes a convenient means for suspending the device from a hook or other supporting member in a location which is readily accessible to an operator needing it.

THE MODIFICATION

FIGS. 5, 6, and 7 illustrate the device as modified for alleviation of a heart failure by starting blood circulation. The modified device includes many of the essential elements of FIGS. 1 to 4 and they have been so designated. Thus mask 10 and tube 45 are the same. Cylinder 16 has been replaced by a cylinder 48 of a capacity much greater than that of cylinder 16. This cylinder 48 has a capacity of about 6 liters.

Because of this capacity cylinder 48 is much longer than cylinder 16 and the piston is not as suitable for one handed operation as in FIGS. 1 to 4. Cross pin 29 of FIG. 2 is replaced by a large cross piece 49 which serves as a base for a guide rod 50 which extends vertically and centrally from cross piece 49 for the full length of cylinder 48. Piston 23 has the same tubular rod 25 but the bore of the latter is continued through piston 23 so that guide 50 is received in tubular rod 25.

It is believed that the piston pump of FIGS. 5 and 6 will require a two handed operation. Thus handle 51 at the end of rod 25 is designed for full grip as compared to the finger engagement intended for handle 26 and U frame 30 is replaced by a handle 52 outstanding from cylinder 48. Cylinder 48 has a bleed hole 44 the same as in cylinder 16. Piston 23 of FIG. 6 is provided with pressure and relief valves 55 and 56.

A human body is depicted in FIG. 7 as having lungs 53 which communicate with the mouth and nasal passages via a trachea. A heart is shown at 54 in close proximity to lungs 53. The lungs of an adult human being have a capacity slightly less than 6 liters. Thus with mask 10 of the device of FIG. 5 and 6 applied over the nose and mouth of a person having heart failure an operator grasps handle 51 with one hand and handle 52 with the other hand. Piston 23 is then reciprocated in cylinder 48 to substantially the full length of cylinder 48.

On the instroke or piston 23 lungs 53 are filled to the limit of their capacity by air under pressure. Thus the lungs are expanded against heart 54 to compress the latter. On the outstroke of piston 23 the lungs contract to relieve the pressure on the heart to permit it to expand to its normal condition. This alternate compression and expansion of heart 54 causes the latter to perform its pumping function to initiate blood circulation. Under many conditions the circulation will be sufficient to sustain life.

Bleed hole 44 in cylinder 48 adds fresh air to the air that is forced into lungs 53 on the instroke of piston 23.

While preferred specific embodiments of the invention are herein disclosed it is to be clearly understood that the invention is not to be limited to the exact conditions, mechanisms, and materials illustrated and described because various modifications may be provided in putting the invention into practice.

What is claimed is

1. In a device for removing an obstruction from the throat of a human being or generating artificial respiration in said being,
   a. a face mask of a flexible material for application over the mouth and nose of said human being including a main body portion and side wall structures having marginal peripheral portions that are pressed against the nose-chin area in airtight relation therewith to define a cavity over said mouth and nose,
b. an opening in said main body portion,
c. a rigid cylinder having one end open and its other end closed by an end wall formed with a central opening in alignment with the opening in the main body portion of the mask,
d. means for securing said end wall to said main body portion,
e. a one way check valve in said end wall offset from said central opening which when open permits passage of air from the interior of said cylinder to the exterior thereof and which when closed inhibits passage of air through the end wall to the interior of said cylinder,
f. a moveable detent means on said end wall for holding said check valve in closed position,
g. a piston reciprocal in said cylinder,
h. said piston having an orifice together with a safety valve controlling the passage of air through said orifice which opens when a safe limit of suction is reached on an outstroke of said piston,
i. a rod upstanding from said piston centrally thereof and projecting beyond the open end of the cylinder when the piston is in its innermost position,
j. a finger engageable handle on the outer end of said rod,
k. spring means biasing said piston towards said end wall whereby instrokes of the piston are powered by said spring means,
l. a frame including a cross-members extending transversely of said open end and mounted on the exterior of said cylinder whereby said member is gripped by the hand of an operator whose fingers are in engagement with said finger engageable member and tightening of the grip of said hand causes an outstroke of said piston against the influence of said spring means,
m. a bleed hole in said cylinder adjacent to said end wall; and
n. a tube secured to said main body portion and communicating with the opening therein, said tube having an extent just long enough to provide for its insertion between the teeth and over the tongue of said human being to function as a gag and tongue depressor.

2. The device of claim 1 in which the means for securing said end wall to the mask comprises a neck depending from the end wall and about said central opening, said neck having an outer annular grove receiving marginal portions of said body portion about the opening therein.

3. The device of claim 1 in which said one way check valve comprises an aperture in the end wall offset from the central opening therein; a plurality of air passages spaced apart and about said aperture, and a valve member consisting of a stem moveable in said aperture, a stop on one end of said stem engageable with the inner surface of said end wall and a disc on the other end of the stem moveable into position closing said air passages by engaging the outer surface of said end wall.

4. The device of claim 3 in which the moveable detent comprises a member pivotally mounted on the underface of said end wall and swingable into and out of position engaging said disc.

5. The device of claim 1 in which the safety valve takes the form of a flap having the properties of flexibility to a required degree and secured at one point to the inner face of said piston.

6. The device of claim 1 in which the rod is tubular and the spring means comprises an expansion coil spring in the tubular rod and having one end anchored to the outer end of the rod and its other end anchored to said end wall.

7. The device of claim 1 in which the finger engageable handle takes the form of a transverse member normal to said rod.

8. The device of claim 7 in which the frame is of inverted U shape and comprises legs having portions secured to the external surface of the cylinder and a crossbar spanning outer ends of said legs and parallel to said transverse member on said rod.

9. The device of claim 8 in which the crossbar has a thumb receiving hole midway its ends.

10. The device of claim 1 in which the tube is perforated.

* * * * *